US010836696B2

(12) United States Patent
Yuan et al.

(10) Patent No.: US 10,836,696 B2
(45) Date of Patent: Nov. 17, 2020

(54) METHOD FOR INCREASING UV TRANSMITTANCE OF ETHYLENE GLYCOL

(71) Applicants: CHANGCHUN MEIHE SCIENCE AND TECHNOLOGY DEVELOPMENT CO., LTD., Luyuan District Changchun, Jilin (CN); THE COCA-COLA COMPANY, Atlanta, GA (US)

(72) Inventors: Yi Yuan, Jilin (CN); Haiyu Ren, Atlanta, GA (US)

(73) Assignees: The Coca-Cola Company, Atlanta, GA (US); Changchun Meihe Science and Technology Development Co., Ltd., Jilin (CN)

( * ) Notice: Subject to any disclaimer, the term of this patent is extended or adjusted under 35 U.S.C. 154(b) by 0 days.

(21) Appl. No.: 16/090,345

(22) PCT Filed: Mar. 30, 2017

(86) PCT No.: PCT/CN2017/078746
§ 371 (c)(1),
(2) Date: Oct. 1, 2018

(87) PCT Pub. No.: WO2017/167219
PCT Pub. Date: Oct. 5, 2017

(65) Prior Publication Data
US 2019/0112248 A1   Apr. 18, 2019

(30) Foreign Application Priority Data
Mar. 30, 2016 (CN) .......................... 2016 1 0191715

(51) Int. Cl.
C07C 29/90 (2006.01)
B01J 23/888 (2006.01)
B01J 23/835 (2006.01)
C07C 29/141 (2006.01)
B01J 23/887 (2006.01)

(52) U.S. Cl.
CPC ............. *C07C 29/90* (2013.01); *B01J 23/835* (2013.01); *B01J 23/888* (2013.01); *B01J 23/8875* (2013.01); *B01J 23/8885* (2013.01); *C07C 29/141* (2013.01); *B01J 2523/305* (2013.01); *B01J 2523/31* (2013.01); *B01J 2523/43* (2013.01); *B01J 2523/51* (2013.01); *B01J 2523/68* (2013.01); *B01J 2523/69* (2013.01); *B01J 2523/847* (2013.01); *Y02P 20/52* (2015.11)

(58) Field of Classification Search
None
See application file for complete search history.

(56) References Cited

U.S. PATENT DOCUMENTS

| 4,358,625 A | 11/1982 | Paggini et al. | |
| 4,830,712 A * | 5/1989 | Crandall | C07C 29/80 |
| | | | 203/3 |
| 2008/0207953 A1 * | 8/2008 | Houssin | B01J 23/72 |
| | | | 568/420 |

FOREIGN PATENT DOCUMENTS

| CN | 101032688 | 9/2007 | |
| CN | 101058526 | 10/2007 | |
| CN | 103721717 | 4/2014 | |
| CN | 104109081 A * | 10/2014 | C07C 29/90 |
| CN | 101309749 | 11/2018 | |
| DE | 1025852 | 3/1958 | |
| WO | WO 2016045584 | 3/2016 | |

OTHER PUBLICATIONS

Translation of International Preliminary Report on Patentability for PCT/CN2017/078746, dated Jun. 21, 2017.
Extended European Search Report for EP 17773249.2, dated Dec. 3, 2019.

* cited by examiner

Primary Examiner — Rosalynd A Keys
(74) Attorney, Agent, or Firm — King & Spalding

(57) ABSTRACT

The present invention provides a method for increasing the UV transmittance of ethylene glycol. The method uses an ethylene glycol solution and hydrogen as raw materials, and uses an alloy catalyst comprising nickel, one or more rare-earth elements, tin, and aluminum, the contents thereof in parts by weight being 10-90, 1-5, 1-60, and 5-9, respectively. The method of the present invention uses an inexpensive, stable-in-aqueous-phase, carrier-free alloy as a catalyst, and continuously adds hydrogen to reduce unsaturated impurities in ethylene glycol. In application of the method of the present invention in continuous industrial-scale production, the use of this type of alloy catalyst could be especially significant for the achievement of long-term system stability and control of production costs.

11 Claims, 1 Drawing Sheet

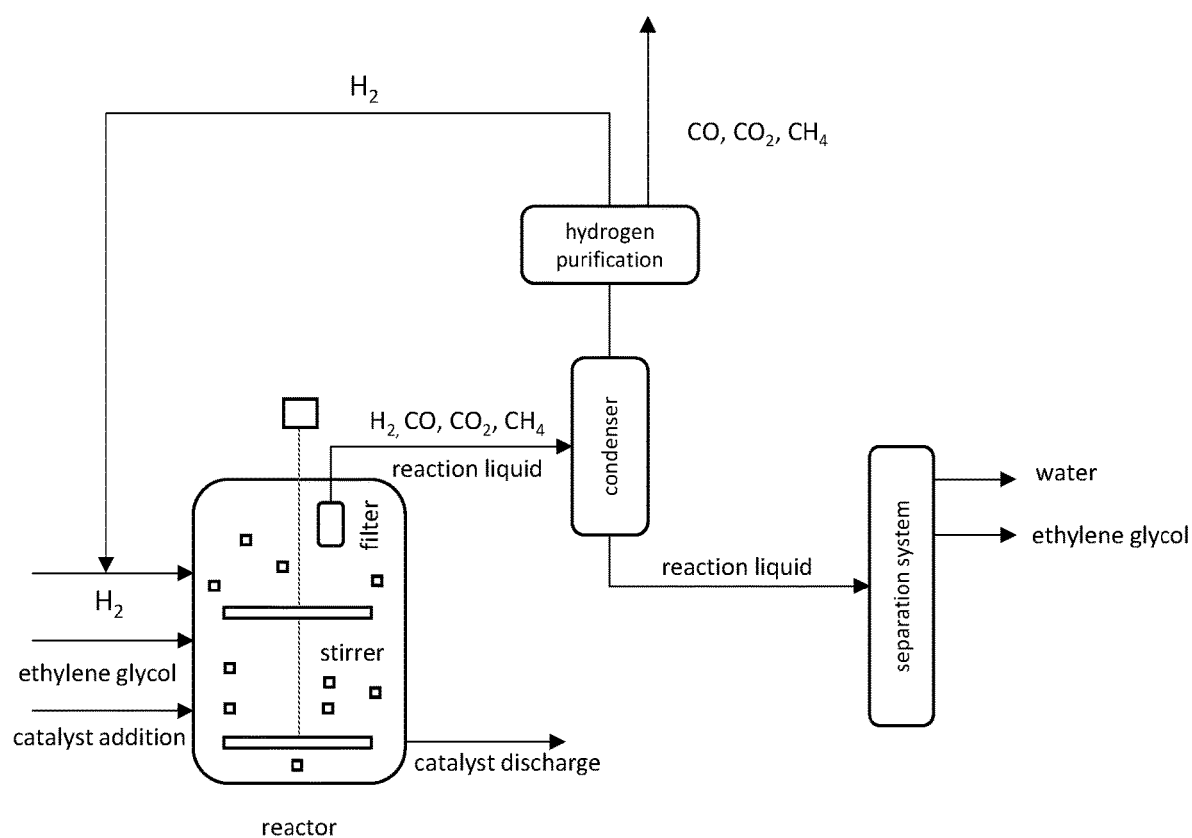

METHOD FOR INCREASING UV TRANSMITTANCE OF ETHYLENE GLYCOL

TECHNICAL FIELD

The present invention relates to the field of ethylene glycol production in chemical industry, in particular to a method for removing impurities in ethylene glycol.

BACKGROUND ART

Ethylene glycol has a large application market as an important monomer for bottle-grade polyesters and fiber-grade polyesters. Ethylene glycol can be produced by two routes: in one route, a petroleum-based olefin or a bio-olefin is used as a starting material, and an oxidation and hydration method is employed; in another route, an oxalate ester is used as a starting material, and a hydrogenation method is employed.

The main source of impurities affecting the quality of an ethylene glycol product is oxidation by-products in an ethylene oxidation process (e.g. acrolein, crotonaldehyde, etc.), or acids, aldehydes or esters produced during hydrogenation of an oxalate ester. In the middle and late stages of catalyst use in particular, the diversity and quantity of these by-products will increase as the reaction temperature increases. The ultraviolet transmittance (UV value) of the product is widely used internationally as a general index for judging the quality of the ethylene glycol product; a method in common use is to determine the UV transmittance of ethylene glycol for wavelengths in the range of 220 nm-350 nm, in order to detect the content of impurities in the ethylene glycol. These impurities will significantly reduce the UV transmittance of ethylene glycol at 220-350 nm, i.e. the UV transmittance reflects the amount of impurities in the ethylene glycol. Ethylene glycol with an unsatisfactory UV value will affect the quality of downstream polyester products, including strength, color and dyeing, etc. It is very difficult for impurities affecting the UV transmittance of ethylene glycol to be removed by a rectification method; in general, physical methods and chemical methods are used to remove impurities. The main physical methods are adsorption and membrane separation; the main chemical method is the method of catalytic hydrogenation.

Said adsorption includes activated carbon adsorption and resin adsorption. Since activated carbon adsorption has a limited capacity, resin adsorption is generally used in industry, but resin regeneration will produce a lot of acidic/alkaline waste liquid; in particular, when the ethylene glycol contains a large amount of unsaturated compounds, resin regeneration processes will be carried out more frequently.

Relatively speaking, catalytic hydrogenation in which most of the unsaturated compounds are hydrogenated is more economical and environmentally friendly. The majority of commonly used technologies for increasing the UV transmittance of ethylene glycol by hydrogenation use a fixed-bed catalyst, e.g. the patents CN201310129838.6, CN201310078821.2, CN200710021418.0, CN201310379199.9, CN200710021425.0, CN201310732399.8, CN201110045256.0 and CN201410117718.9. Since inorganic oxides such as alumina and silica are generally used as supports for fixed-bed catalysts, these supports are unstable in the aqueous phase; ethylene glycol readily undergoes intermolecular dehydration, and the water produced is not favorable for long-term stable operation of the fixed-bed catalyst. For example, in the process of producing ethylene glycol from ethylene, a multiple-effect evaporator kettle liquid (85% ethylene glycol) has a water content of 15%, and it is generally necessary to first of all remove the 15% water by rectification and then perform catalytic reduction of impurities in the ethylene glycol solution, in order to reduce the instability of the catalyst in water. Such operations are cumbersome and energy-consuming.

Direct treatment of a water-containing ethylene glycol solution, without the need to completely remove the water in the ethylene glycol solution by rectification, would be more economical and environmentally friendly; this would necessitate the selection of a catalyst that is stable in the aqueous phase. Metal alloy catalysts are one type of catalyst that is stable in the aqueous phase. For example, the patent U.S. Pat. No. 4,647,705 uses an aluminum-nickel alloy to treat an ethylene glycol solution; the reaction time is as long as 3 hours, causing an increase in the duration, energy consumption and costs of large-scale industrial production. Furthermore, when such a catalyst reaction is complete, it is also necessary to separate the alloy from the ethylene glycol, so the number of operational steps is increased.

In order to avoid the separation of alloy from ethylene glycol, a metal alloy can also be used as a fixed-bed catalyst in the treatment of unsaturated impurities in an ethylene glycol solution by continuous hydrogenation. CN101032688 uses a fixed bed with an aluminum-nickel alloy as a framework for the treatment of ethylene glycol by continuous hydrogenation; the catalyst preparation method uses alkaline liquid heating and only 8-30% of the aluminum is removed, with the remaining 70-92% of the aluminum still being present in the form of aluminum-nickel alloy. In CN200710021418, a 1-3 mm particulate nickel-aluminum alloy with no aluminum removed is used directly as a fixed-bed catalyst to treat an ethylene glycol solution. The surface area of the nickel-aluminum alloy fixed-bed catalyst is very small, most of the nickel is unable to have a catalytic action, and at the same time, due to irregularity of shape, drift flow of liquid in the catalyst bed layer readily occurs.

In order to avoid the instability of a catalyst support in the aqueous phase, an organic polymer that is stable in the aqueous phase may be used as a support, e.g. a polyolefin, polyamide, polycarbonate or other resin, or a modified product thereof; for example, in the patent CN104418704, each Raney Ni metal alloy particle has a part thereof embedded in a resin, and this embedded part of the Ni is unable to have a catalytic action, so that the catalytic efficiency is reduced. In CN104945227A, continuous-phase carbon and dispersed-phase Raney alloy particles are used, wherein the dispersed-phase Raney alloy particles are uniformly or non-uniformly dispersed in the continuous-phase carbon. However, the continuous carbon phase is obtained by high-temperature roasting of an organic polymer, and the catalyst preparation process consumes a large amount of energy.

Furthermore, if a reaction liquid has alkaline conditions, the hydrogenation activity of a metal catalyst will be increased; for example, in CN101199930A, a metal alloy catalyst is used for the conversion of sorbitol by hydrogenation in alkaline conditions. However, in alkaline hydrogenation conditions, ethylene glycol readily produces new by-products, affecting the UV transmittance of the ethylene glycol.

Thus, there is a need to provide a method for improving the UV transmittance of ethylene glycol by continuous hydrogenation in an aqueous phase; the method makes direct use of a metal alloy catalyst which is stable in the aqueous phase and is capable of treating unsaturated matter in ethylene glycol by hydrogenation.

CONTENT OF THE INVENTION

A first technical problem to be solved by the present invention is to provide a method for improving the ultraviolet transmittance of ethylene glycol; the method can make direct use of a metal alloy catalyst which is capable of treating unsaturated matter in ethylene glycol by hydrogenation, and can continuously carry out a catalytic hydrogenation reaction; the metal alloy catalyst is stable in an acidic or neutral aqueous solution, and is suitable for long-term stable operation in neutral and acidic conditions.

A method for improving the ultraviolet transmittance of ethylene glycol, the method using an ethylene glycol solution and hydrogen as starting materials, and using a metal alloy catalyst;

the metal alloy catalyst comprises nickel, one or more rare earth element, tin and aluminum, the contents of the components in parts by weight being 10-90 parts, 1-5 parts, 1-60 parts and 5-9 parts respectively.

The term "rare earth elements" is a general designation for the 17 chemical elements having atomic numbers 21, 39 and 57-71 in group IIIB of the periodic table, including lanthanum (La), cerium (Ce) and samarium (Sm), etc.

The metal alloy is a water-insoluble alloy. The metal alloy catalyst is stable in an aqueous solution of pH 3-7.

In one embodiment, the metal alloy catalyst comprises nickel, one or more rare earth element, tin, aluminum and tungsten, the contents of the components in parts by weight preferably being 10-90 parts, 1-5 parts, 1-60 parts, 5-9 parts and 1-90 parts respectively.

In one embodiment, the metal alloy catalyst comprises nickel, one or more rare earth element, tin, aluminum, tungsten and molybdenum, the contents of the components in parts by weight preferably being 10-90 parts, 1-5 parts, 1-60 parts, 5-9 parts, 1-90 parts and 0.5-20 parts respectively.

In one embodiment, the metal alloy catalyst comprises nickel, one or more rare earth element, tin, aluminum, tungsten, molybdenum, and boron or phosphorus, the contents of the components in parts by weight preferably being 10-90 parts, 1-5 parts, 1-60 parts, 5-9 parts, 1-90 parts, 0.5-20 parts and 0.01-5 parts respectively.

In the metal alloy catalyst, the various element components together act to catalyze hydrogenation; the surface area of the catalyst is effectively increased, and the catalytic efficiency is increased.

Preferably, the reaction carried out is in a continuous mode. Preferably, the amount used of the metal alloy catalyst is 0.01-10 times the amount fed of the ethylene glycol solution.

The method further comprises the addition of ethylene glycol solution and metal alloy catalyst at any time. The amount added of the metal alloy catalyst is: 0.01-5 kg of metal alloy catalyst added per 1000 kg of ethylene glycol fed. A method of adding metal alloy catalyst may be realized by discharging a portion of old catalyst through a catalyst discharge valve (generally at the bottom of a reactor), and then adding an equal amount of new catalyst through a catalyst feed valve (generally at the bottom of the reactor).

The metal alloy catalyst is added to the reactor after being mixed with water. In one example, the method is as follows: before the reaction starts, a metal alloy catalyst is added to a slurry-bed reactor, a reaction kettle is sealed, hydrogen is passed in at atmospheric pressure to replace air in the reaction kettle, then the hydrogen pressure is increased to a required pressure, hydrogen continues to be passed in, the reaction kettle temperature rises to a required temperature, and continuous feeding begins. A pump is used to add ethylene glycol to the reactor, and a reaction is carried out; a reaction liquid flows continuously out of the reactor. As the reaction proceeds, it is necessary to add ethylene glycol and metal alloy catalyst at any time; the addition of ethylene glycol and metal alloy catalyst is in a continuously flowing state. Preferably, a filter is installed in the reactor, for the purpose of retaining metal alloy catalyst in the reactor, such that the metal alloy catalyst is not carried away by gas and reaction liquid flowing out through the filter. The gas and reaction liquid will flow out continuously through the filter and then enter a condenser to undergo gas/liquid separation; crude hydrogen undergoes purification to remove CO, $CO_2$ and $CH_4$, etc., to become pure hydrogen again, and returns to the reactor; a material flowing out of the condenser enters a separation system, and separation is performed to obtain water and ethylene glycol, etc.

The ethylene glycol solution is an aqueous ethylene glycol solution; the ethylene glycol liquid concentration is 5-90 wt %. Preferably, the ethylene glycol solution has a concentration of 50-85 wt %. In a continuous operation, the ethylene glycol solution may be fed continuously by means of a delivery pump.

The method has the following reaction condition: a reaction system temperature is 50-200° C.; preferably, the reaction system temperature is 80-150° C.

Preferably, the method has the following reaction conditions: a reaction temperature of the reaction system is 50-200° C., a reaction pressure is 0.1-12 MPa, and a reaction time is 10 min or more.

More preferably, the method has the following reaction conditions: the reaction temperature of the reaction system is 80-150° C., the reaction pressure is 0.5-10 MPa, and the reaction time is 0.5-3 h. The reaction time is most preferably 0.5-2 hours.

Preferably, the reaction is carried out in a slurry-bed reactor. To ensure that the reaction proceeds smoothly, the total volume of reaction liquid formed does not exceed 80% of the reactor volume.

Preferably, a starting material of the ethylene glycol solution may come from petroleum, coal base or biomass.

The present invention has the following beneficial effects:

The method of the present invention uses an inexpensive alloy, which is stable in the aqueous phase and does not require a support, as a catalyst, in the continuous hydrogenation/reduction of unsaturated impurities in ethylene glycol. When the method of the present invention is applied in continuous industrial production, the use of this alloy catalyst is of particular importance for the long-term stable operation of the system and the control of production costs.

DESCRIPTION OF THE ACCOMPANYING DRAWING

Particular embodiments of the present invention are explained in further detail below with reference to the accompanying drawing.

FIG. 1 shows an ethylene glycol hydrogenation process flow.

PARTICULAR EMBODIMENTS

In order to explain the present invention more clearly, the present invention is explained further below with reference to preferred examples and the accompanying drawing. Similar components in the drawing are represented by identical reference labels. Those skilled in the art should understand that the content specifically described below is illustrative but non-limiting, and should not be used to restrict the scope of protection of the present invention.

Example 1

Preparation of Metal Alloy Catalyst

For the metal alloy catalyst of the present invention, a chemical reduction method or an electrolytic deposition method may be used to directly prepare an active metal powder having a high specific surface area, or a smelting method is first used to form a metal alloy, then a mechanical pulverizing method or atomization method etc. is used to form a metal powder, and finally a conventional Raney nickel catalyst activation method is used to form an active metal powder. For example, nickel, a rare earth element, tin, aluminum, tungsten, molybdenum, and boron or phosphorus are added to a smelting furnace, the contents thereof in parts by weight being 10-90 parts, 1-5 parts, 1-60 parts, 5-9 parts, 1-90 parts, 0.5-20 parts and 0.01-5 parts respectively, the temperature is increased to 1500-2000° C., then the temperature is reduced, thorough mechanical stirring is carried out to achieve uniformity and then the furnace is emptied, to obtain a metal alloy. A hammer mill is used to pulverize the metal alloy into a metal powder, and the metal powder is immersed in a 20 wt %-25 wt % aqueous sodium hydroxide solution for 1-2 hours at 70-95° C., to form an active metal powder having a high specific surface area.

A metal alloy catalyst Ni80La1Sn30Al5 (indicating a metal alloy composition of 80 parts Ni+1 part La+30 parts Sn+5 parts Al, similarly below), a metal alloy catalyst Ni10Sm5Sn3Al9W70Mo5, a metal alloy catalyst Ni70Ce1Sn50Al7W5Mo1B5, a metal alloy catalyst Ni90Ce3Sn60Al9W20Mo5B1, a metal alloy catalyst Ni10Sm5Sn10Al9W90, a metal alloy catalyst Ni90Ce3Sn60Al9W20Mo20P0.01 and a metal alloy catalyst Ni80La1Ce0.5Sn30Al5 are separately prepared.

Example 2

6 L of water and 1000 g of the metal alloy catalyst Ni80La1Sn30Al5 are added to a 10 L reaction kettle while stirring. The reaction kettle is sealed, hydrogen is passed in at the rate of 100 L/h at atmospheric pressure to replace air in the reaction kettle for 5 hours, then the hydrogen pressure is increased to 10 MPa, hydrogen continues to be passed in for 5 hours, the temperature of the reaction kettle is increased to 80° C., and continuous feeding begins. The feed composition is: 50 wt % ethylene glycol and 50 wt % water; the feeding rate is 3 L/h. The residence time of the aqueous ethylene glycol solution in the reaction kettle is 2 hours. Hydrogen and a reaction liquid resulting from a reaction flow out of the reaction kettle through a filter and enter a condensation tank; the discharge rate of the reaction liquid is 3 L/h; the reaction liquid is cooled and then discharged from the bottom of the condensation tank, to obtain an outflowing liquid. The outflowing liquid enters a rectification separation system, and water and ethylene glycol are separately obtained. A sample is taken at the bottom of the condensation tank, and a UV/vis spectrophotometer is used to detect the UV transmittance of the ethylene glycol. See table 1 for the results.

The metal catalyst of the present invention can ensure that the reaction system continuously operates for 1000 hours or more, and the UV transmittance of ethylene glycol is still stable.

Example 3

The metal alloy catalyst is Ni10Sm5Sn3Al9W70Mo5, and the amount added is 5000 g. The feed composition is: 70 wt % ethylene glycol. The reaction pressure is 0.5 MPa, the reaction temperature is 150° C., and the other operating conditions are the same as in example 2. See table 1 for results.

The metal catalyst of the present invention can ensure that the reaction system continuously operates for 1000 hours or more, and the UV transmittance of ethylene glycol is still stable.

Example 4

The metal alloy catalyst is Ni70Ce1Sn50Al7W5Mo1B5, and the amount added is 500 g. The feed composition is: 85 wt % ethylene glycol. The reaction pressure is 12 MPa, the reaction temperature is 170° C., and the other operating conditions are the same as in example 2. See table 1 for results.

The metal catalyst of the present invention can ensure that the reaction system continuously operates for 1000 hours or more, and the UV transmittance of ethylene glycol is still stable.

Example 5

The metal alloy catalyst is Ni90Ce3Sn60Al9W20Mo5B1, and the amount added is 1000 g. The feed composition is: 75 wt % ethylene glycol. The reaction pressure is 5 MPa, the reaction temperature is 90° C., and the other operating conditions are the same as in example 2. See table 1 for results. After 1000 hours of catalyst operation, the UV transmittance of ethylene glycol is still stable.

Example 6

The metal alloy catalyst is Ni90Ce3Sn60Al9W20Mo5B1, and the amount added is 5000 g. The feed composition is: 70 wt % ethylene glycol, the reaction pressure is 1 MPa, the reaction temperature is 100° C., and the other operating conditions are the same as in example 2. See table 1 for results.

The metal catalyst of the present invention can ensure that the reaction system continuously operates for 1000 hours or more, and the UV transmittance of ethylene glycol is still stable.

Example 7

The alloy main catalyst is Ni10Sm5Sn10Al9W90, and the amount added is 180 g. The feed composition is: 70 wt % ethylene glycol. The reaction pressure is 8 MPa and the reaction temperature is 140° C. The other operating conditions are the same as in example 2. See table 1 for results.

The metal catalyst of the present invention can ensure that the reaction system continuously operates for 1000 hours or more, and the UV transmittance of ethylene glycol is still stable.

Example 8

The alloy catalyst is Ni90Ce3Sn60Al9W20Mo20P0.01, and the amount added is 5 g. The feed composition is: 85 wt % ethylene glycol. The reaction pressure is 3 MPa and the reaction temperature is 120° C. The other operating conditions are the same as in example 2. See table 1 for results.

The metal catalyst of the present invention can ensure that the reaction system continuously operates for 1000 hours or more, and the UV transmittance of ethylene glycol is still stable.

TABLE 1

Effect of hydrogenation treatment of ethylene glycol on UV transmittance

| | Pressure (MPa) | Temp. (° C.) | Water content of ethylene glycol (%) | | UV transmittance (%) | | |
|---|---|---|---|---|---|---|---|
| | | | | | 220 nm | 274 nm | 350 nm |
| Example 2 | 10 | 80 | 50 | After hydrogenation | 47 | 89 | 100 |
| | | | | Before hydrogenation | 36 | 81 | 100 |
| Example 3 | 0.5 | 150 | 30 | After hydrogenation | 67 | 96 | 100 |
| | | | | Before hydrogenation | 46 | 90 | 100 |
| Example 4 | 12 | 170 | 15 | After hydrogenation | 63 | 95 | 100 |
| | | | | Before hydrogenation | 50 | 90 | 100 |
| Example 5 | 5 | 90 | 25 | After hydrogenation | 76 | 100 | 100 |
| | | | | Before hydrogenation | 62 | 92 | 100 |
| Example 6 | 1 | 100 | 30 | After hydrogenation | 25 | 70 | 86 |
| | | | | Before hydrogenation | 0.2 | 16 | 86 |
| Example 7 | 8 | 140 | 30 | After hydrogenation | 52 | 83 | 100 |
| | | | | Before hydrogenation | 3 | 75 | 86 |
| Example 8 | 3 | 120 | 15 | After hydrogenation | 65 | 95 | 100 |
| | | | | Before hydrogenation | 36 | 88 | 100 |

Clearly, the above examples of the present invention are merely examples given for the purpose of clearly explaining the present invention, and do not limit the embodiments of the present invention. Those skilled in the art could still make other changes or alterations in various forms, on the basis of the above explanation. It is not possible to set out all embodiments here exhaustively. All obvious changes or alterations derived from the technical solution of the present invention shall still fall within the scope of protection of the present invention.

The invention claimed is:

1. A method for improving the ultraviolet transmittance of ethylene glycol, the method comprising contacting an ethylene glycol solution and hydrogen with one of the following catalysts:
   (i) an unsupported metal alloy catalyst consisting of nickel, one or more rare earth element, tin and aluminum, the contents of the components in parts by weight being 10-90 parts, 1-5 parts, 1-60 parts and 5-9 parts respectively,
   (ii) an unsupported catalyst consisting of nickel, one or more rare earth element, tin, aluminum and tungsten, the contents of the components in parts by weight being 10-90 parts, 1-5 parts, 1-60 parts, 5-9 parts and 1-90 parts respectively;
   (iii) an unsupported catalyst consisting of nickel, one or more rare earth element, tin, aluminum, tungsten and molybdenum, the contents of the components in parts by weight being 10-90 parts, 1-5 parts, 1-60 parts, 5-9 parts, 1-90 parts and 0.5-20 parts respectively; or
   (iv) an unsupported catalyst consisting of nickel, one or more rare earth element, tin, aluminum, tungsten, molybdenum and boron or phosphorous, the contents of the components in parts by weight being 10-90 parts, 1-5 parts, 1-60 parts, 5-9 parts, 1-90 parts, 0.5-20 parts and 0.01-5 parts respectively.

2. The method as claimed in claim 1, characterized in that the amount used of the catalyst is 0.01-10 times the mass fed of the ethylene glycol solution.

3. The method as claimed in claim 1, characterized in that the method further comprises the addition of ethylene glycol solution and metal alloy catalyst at any time; the amount added of the metal alloy catalyst is: 0.01-5 kg of metal alloy catalyst added per 1000 kg of ethylene glycol fed.

4. The method as claimed in claim 1, characterized in that the method has a reaction system temperature of 50-200° C.

5. The method as claimed in claim 4, characterized in that the method has a reaction pressure of 0.1-12 MPa, and a reaction time of 10 min or more.

6. The method as claimed in claim 5, characterized in that the reaction system temperature is 80-150° C., the reaction pressure is 0.5-10 MPa, and the reaction time is 0.5-3 h.

7. The method as claimed in claim 1, characterized in that the ethylene glycol solution has a concentration of 5-90 wt.

8. The method as claimed in claim 1, wherein catalyst (i) or (ii) is selected from the group consisting of Ni80La1Sn30Al5, Ni10Sm5Sn3Al9W70Mo5, Ni70Ce1Sn50Al7W5Mo1B5, Ni90Ce3Sn60Al9W20Mo5B1, Ni10Sm5Sn10Al9W90, Ni90Ce3Sn60Al9W20Mo20P0.01 and Ni80La1Ce0.5Sn30Al5.

9. The method as claimed in claim 4, wherein the method has a reaction system temperature of 80-150° C.

10. The method as claimed in claim 6, wherein the reaction time is 0.5-2 hours.

11. The method as claimed in claim 7, wherein the ethylene glycol solution has a concentration of 50-85 wt %.

* * * * *